US011278182B2

(12) United States Patent
Popovic et al.

(10) Patent No.: US 11,278,182 B2
(45) Date of Patent: Mar. 22, 2022

(54) ENHANCED VISUALIZATION OF BLOOD VESSELS USING A ROBOTICALLY STEERED ENDOSCOPE

(71) Applicant: KONINKLIJKE PHILIPS N.V., Eindhoven (NL)

(72) Inventors: Aleksandra Popovic, New York, NY (US); Haytham Elhawary, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 546 days.

(21) Appl. No.: 14/402,138

(22) PCT Filed: Jun. 20, 2013

(86) PCT No.: PCT/IB2013/055070
§ 371 (c)(1),
(2) Date: Nov. 19, 2014

(87) PCT Pub. No.: WO2014/001980
PCT Pub. Date: Jan. 3, 2014

(65) Prior Publication Data
US 2015/0112126 A1    Apr. 23, 2015

Related U.S. Application Data

(60) Provisional application No. 61/665,375, filed on Jun. 28, 2012.

(51) Int. Cl.
*A61B 1/00*    (2006.01)
*A61B 1/313*    (2006.01)
(Continued)

(52) U.S. Cl.
CPC .......... *A61B 1/00006* (2013.01); *A61B 1/005* (2013.01); *A61B 1/00009* (2013.01);
(Continued)

(58) Field of Classification Search
CPC . A61B 1/00045; A61B 1/0005; A61B 5/7425; A61B 5/7485; A61B 1/00009;
(Continued)

(56) References Cited

U.S. PATENT DOCUMENTS 6,006,127 A * 12/1999 Van Der Brug .. A61M 25/0105
600/426
6,201,984 B1    3/2001 Funda
(Continued)

FOREIGN PATENT DOCUMENTS

EP    1892009    2/2008
JP    8511694 A    12/1996
(Continued)

*Primary Examiner* — Ryan N Henderson
*Assistant Examiner* — Pamela F Wu

(57) ABSTRACT

A system for visualizing an anatomical target includes a scope for internal imaging having a field of view less than a region to be imaged. A planning module is configured to receive video from the scope such that field of view images of the scope are stitched together to generate a composite image of the region to be imaged. An image guidance module is configured to move the scope along the anatomical target during a procedure such that an image generated in the field of view of the scope is displayed as live video overlaid on a field of the composite image.

10 Claims, 4 Drawing Sheets

(51) Int. Cl.
  *A61B 34/30* (2016.01)
  *A61B 1/005* (2006.01)
  *A61B 1/04* (2006.01)
  *A61B 5/00* (2006.01)
  *A61F 2/06* (2013.01)
  *G06T 11/60* (2006.01)
  *A61B 90/00* (2016.01)

(52) U.S. Cl.
  CPC ...... *A61B 1/00045* (2013.01); *A61B 1/00147* (2013.01); *A61B 1/00149* (2013.01); *A61B 1/00172* (2013.01); *A61B 1/04* (2013.01); *A61B 1/3132* (2013.01); *A61B 5/489* (2013.01); *A61B 34/30* (2016.02); *A61F 2/062* (2013.01); *G06T 11/60* (2013.01); *A61B 2034/302* (2016.02); *A61B 2090/365* (2016.02); *G06T 2210/41* (2013.01)

(58) Field of Classification Search
  CPC ............. A61B 5/743; A61B 1/00149; A61B 2034/2055; A61B 2034/2065; A61B 2034/303; A61B 2090/364; A61B 2034/302; A61B 1/01; A61B 34/30
  USPC .......................................... 382/173; 600/117
  See application file for complete search history.

(56) References Cited

U.S. PATENT DOCUMENTS

| | | | |
|---|---|---|---|
| 8,200,042 B2* | 6/2012 | Doi | A61B 1/00022 382/173 |
| 2004/0210105 A1 | 10/2004 | Hale et al. | |
| 2007/0060792 A1 | 3/2007 | Draxinger et al. | |
| 2007/0167801 A1 | 7/2007 | Webler | |
| 2008/0033240 A1* | 2/2008 | Hoffman | A61B 34/70 600/109 |
| 2008/0243142 A1* | 10/2008 | Gildenberg | A61B 90/36 606/130 |
| 2009/0005640 A1 | 1/2009 | Fahre et al. | |
| 2009/0208143 A1* | 8/2009 | Yoon | A61B 1/0058 382/321 |
| 2009/0259102 A1* | 10/2009 | Koninckx | A61B 1/00181 600/111 |
| 2010/0249506 A1 | 9/2010 | Prisco | |
| 2010/0249507 A1* | 9/2010 | Prisco | A61B 1/00009 600/117 |
| 2011/0128352 A1 | 6/2011 | Higgins | |
| 2012/0188352 A1* | 7/2012 | Wittenberg | A61B 90/36 348/65 |
| 2012/0294498 A1* | 11/2012 | Popovic | A61B 1/0005 382/128 |
| 2013/0038707 A1* | 2/2013 | Cunningham | A61B 1/0005 348/65 |
| 2013/0046137 A1* | 2/2013 | Zhao | A61B 1/00181 600/102 |
| 2013/0329020 A1* | 12/2013 | Kriveshko | A61B 1/00009 348/50 |

FOREIGN PATENT DOCUMENTS

| | | |
|---|---|---|
| WO | 2012001549 A1 | 1/2012 |
| WO | 2012035492 A1 | 3/2012 |

\* cited by examiner

ENHANCED VISUALIZATION OF BLOOD VESSELS USING A ROBOTICALLY STEERED ENDOSCOPE

CROSS-REFERENCE TO PRIOR APPLICATIONS

This application is the U.S. National Phase application under 35 U.S.C. § 371 of International Application No. PCT/IB2013/055070, filed on Jun. 20, 2013, which claims the benefit of U.S. Provisional Patent Application No. 61/665,375, filed on Jun. 28, 2012. These applications are hereby incorporated by reference herein.

This disclosure relates to medical instruments and methods and, more particularly, to systems and methods for improved visualization of internal anatomy in medical applications.

Coronary artery bypass grafting (CABG) is a surgical procedure for revascularization of obstructed coronary arteries. In conventional surgery, the patient's sternum is opened, and the heart is fully exposed. However, minimally invasive (MI) bypass surgery is performed through small ports. An important part of a CABG procedure is the removal of a vessel from the patient's body, which is then used to bypass one or more atherosclerotic narrowings in the coronary arteries. The vessel most commonly removed and used is an Internal Mammary Artery (IMA), which may include a Left IMA (LIMA) or Right IMA (RIMA), which are located in the thoracic cavity.

During MI cardiac bypass surgery direct access to these vessels is not available, and they are removed using long instruments inserted into ports through intercostal muscles in spaces between the ribs. During MI surgery, a surgical assistant can hold the endoscope, or it can be held using robotic guidance. In the case of robotic guidance, visual servoing can be used to move the robot to a specific location. Visual servoing consists of selecting a point on the endoscope image, with the robot moving in such a way that the point becomes located in the center of the image.

IMA takedown is usually the most time consuming part of the CABG procedure. IMA takedown usually takes between 45-60 minutes, and the success of a bypass procedure usually depends on the quality of the harvested vessel.

The main challenges during this stage of procedure include the following. Endoscope images are the only visualization method for this procedure, but the endoscope provides only a limited view of a small segment of a blood vessel. For MI, a surgeon works with elongated instruments inserted between the ribs reaching below the sternum area. This makes it difficult since the artery being harvested needs to be carefully isolated from surrounding tissue and side branches have to be cauterized.

A length of, e.g., the LIMA artery has to be sufficient to reach the bypass location on the coronary artery. It is very difficult to estimate the length of the harvested vessel artery during MI procedures (as opposed to open surgery, where the length can be estimated since all areas are visible and accessible). As the LIMA is removed from the middle and inferior part of the chest, it tends to be more embedded in the tissue, slowing down isolation and making visualization of the artery and side branches even more challenging.

The combination of technical difficulties for artery isolation and the unknown length needed for bypass contributes to an extended procedure time, as the surgeon either isolates a much longer arterial segment than needed in the more challenging distal area, or isolates too short a segment, which requires returning later for continued isolation of the artery.

In accordance with an exemplary embodiment of the present invention, described herein is a system for visualizing an anatomical target includes a scope for internal imaging having a field of view less than a region to be imaged. A planning module is configured to receive video from the scope such that field of view images of the scope are stitched together to generate a composite image of the region to be imaged. An image guidance module is configured to move the scope along the anatomical target during a procedure such that an image generated in the field of view of the scope is displayed as live video overlaid on a field of the composite image.

For example, the planning module can be configured to select points of interest in the composite image related to the anatomical target. The system can further include a robot configured to guide the scope and the image guidance module configured to employ the points of interest for guiding the scope. The planning module can be configured to register and overlay operative images over the composite image to provide an enhanced map of the anatomical target. The system can further include a progress indicator displayed with the composite image to indicate progress of the scope, e.g., relative to a total dimension. The anatomical target can include a blood vessel to be isolated and the progress indicator can include a percentage of progress and/or a progress graphic to indicate a portion isolated relative to a total length of the blood vessel. It is also possible that the planning module employs a pre-operative image of the blood vessel to estimate the total length. The anatomical target can include, e.g., an internal mammary artery (IMA) for use in bypass surgery. Further, the scope can include a flexible endoscope.

In accordance with another exemplary embodiment of the present invention, described herein is a system for visualizing an anatomical target that includes a processor and a memory coupled to the processor. The memory includes a planning module configured to stitch together field of view images of an anatomical target received from a scope to form a composite image of the anatomical target. An image guidance module is configured to move the scope along the anatomical target using the composite image such that an image generated in the field of view of the scope is displayed as live video overlaid on a field of the composite image.

For example, the planning module can be configured to select points of interest in the composite image related to the anatomical target. The system can further include a robot configured to guide the scope and the image guidance module configured to employ the points of interest for guiding the scope. The planning module can be configured to register and overlay operative images over the composite image to provide an enhanced map of the anatomical target. The system can further include a progress indicator generated by the image guidance module and displayed with the composite image to indicate progress of the scope, e.g., relative to a total dimension. The anatomical target can include a blood vessel to be isolated and the progress indicator can include a percentage of progress and/or a progress graphic to indicate a portion isolated relative to a total length of the blood vessel. The planning module can employ a pre-operative image of the blood vessel to estimate the total length. The anatomical target can include, e.g., an internal mammary artery (IMA) for use in bypass surgery. Further, the scope can include a flexible endoscope.

In accordance with yet another exemplary embodiment of the present invention, described herein is a method for visualizing an anatomical target, including: imaging portions of an anatomical target using a field of view of a scope; forming a composite image of the anatomical target using the portions; selecting points of interest in the composite image; and from a start point, moving along the anatomical target such that an image generated in the field of view of the scope is displayed as live video overlaid on a field of the composite image.

For example, the method can further include registering and overlaying operative or pre-operative images over the composite image to provide an enhanced map of the anatomical target. Moreover, the method can further generate a progress indicator to indicate progress of the scope relative to a total dimension. The anatomical target can include a blood vessel to be isolated and generating a progress indicator can include indicating a percentage of progress and/or a progress graphic to indicate a portion isolated relative to, e.g., a total length of the blood vessel. Imaging portions of the anatomical target using a field of view of a scope can include robotically moving the scope using the points of interest for guidance. The method can further include moving the scope using visual servoing. It is also possible that the anatomical target includes an internal mammary artery (IMA) and the step of moving along the anatomical target includes isolating the IMA for use in bypass surgery. The method can further include measuring a length of the target anatomy from the composite image.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

Figure 7:
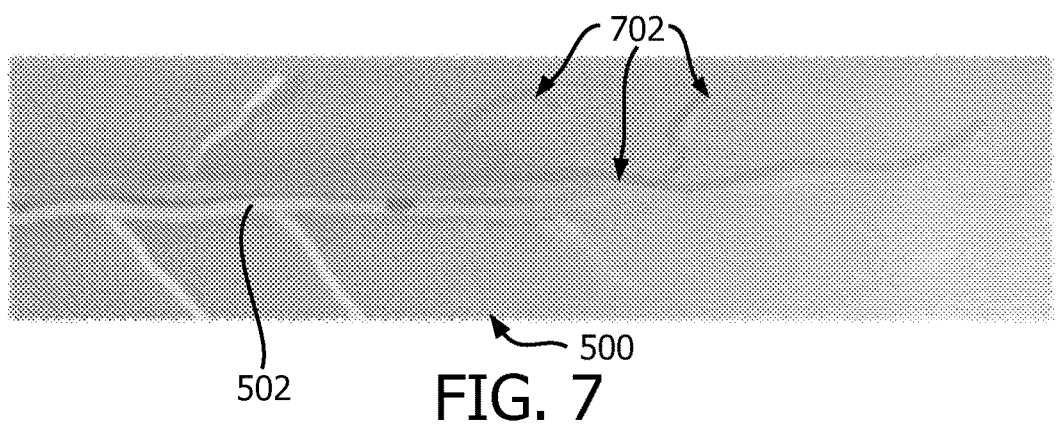
Figure 8:
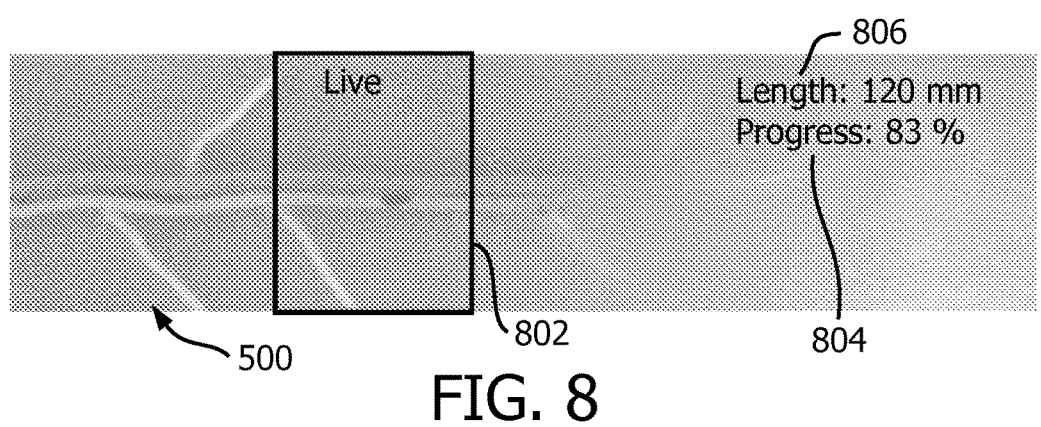

FIG. 7 is an image showing the composite image with registered and overlaid operative images (preoperative and/or intraoperative) of the internal mammary artery in accordance with one embodiment; and FIG. 8 is an image showing the composite image with a live video field of view inset overlaid on the composite image and showing progress (%) and length of the internal mammary artery in accordance with one embodiment.

In accordance with the present principles, a blood vessel isolation planning and execution system is provided to solve the problems of vessel isolation as described above. The present principles provide a significantly enlarged field-of-view showing most of the blood vessel (e.g., the LIMA) as opposed to only a small segment and provide additional information about the blood vessel. This additional information includes, e.g., the length of the blood vessel being isolated for harvesting, the progress of the blood vessel isolation with respect to a desired bypass length and the location of side branches that need to be cauterized.

It should be understood that the present invention will be described in terms of medical instruments for use with and for a coronary bypass procedure; however, the teachings of the present invention are much broader and are applicable to any instrument or procedure where enhanced visualization of a target anatomy is needed or desired. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Figure 1:
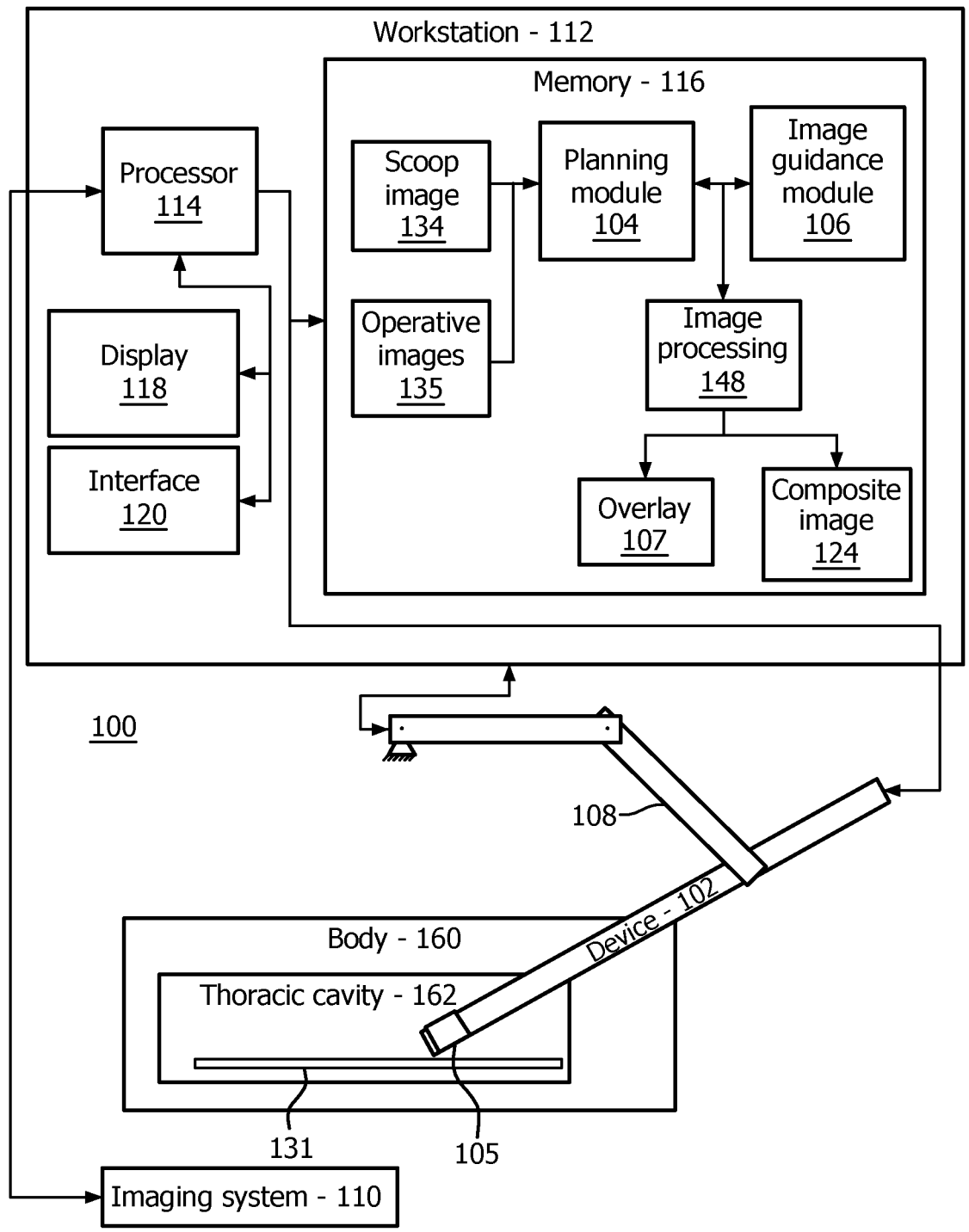
FIG. 1 is a block/flow diagram showing a system for visualizing an anatomical target in accordance with one embodiment.

Referring now to the drawings in which like numerals represent the same or similar elements and initially to FIG. 1, a system 100 for minimally invasive surgery is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store a planning module 104 and an image guidance module 106 employed to work in conjunction with a medical device 102. The medical device 102 may include an imaging device 105 (e.g., camera, fiber optics with lens, etc.) that may be deployed with one or more of a catheter, a guidewire, a probe, an endoscope, a flexible endoscope, a robot, an electrode, a filter device, a balloon device, or other medical component, etc. The device 102 may be inserted into a body 160 of a patient. In one embodiment, a procedure to be performed includes minimally invasive coronary surgery, and the device 102 is inserted into a thoracic cavity 162 of the body 160 to observe and isolate an anatomical target 131, such as a blood vessel (e.g., an IMA).

The planning module 104 includes the following elements and features. During, e.g., a vessel take-down for a coronary bypass procedure, the planning module 104 plans for the control of visualization of a target vessel to be harvested, e.g., the IMA, while permitting a surgeon to manipulate other instruments. The planning module 104 controls image stitching along the IMA to provide a comprehensive field of view, and further provides image registration permitting overlaying of preoperative (or intra-operative) images on, e.g., an endoscope video using methods known in art. The planning module 104 provides for the selection of target points of interest, which can be referred to or indexed for use with the image guidance module 106. The planning module 104 also provides for computation of blood vessel or other anatomical feature lengths (e.g., using the stitched/composite image).

The planning module 104 may be employed to register and overlay operative images 135, such as preoperative or intraoperative images taken using an imaging device 110. The imaging device 110 may be employed contemporaneously or at another time and location to collect the images. The operative images 135 may include three dimensional preoperative computed tomography (CT) images or magnetic resonance images (MRI), etc. or intraoperative X-rays or ultrasound. Other imaging modalities are also contemplated. The operative images 135 may be employed in the overlay image 107 to map out features of the anatomical target 131 that would otherwise be difficult to see in the endoscope images.

The image guidance module 106 provides image-based control of the device 102, e.g., an endoscope, preferably by controlling a robotic system 108, which supports the device 102. The overlay 107 may be generated using an image processing module 148 and the planning module 104. The overlay 107 may include a current live endoscope image 134 visualized on a composite image 124. The composite image 124 is the stitched together view of a plurality of fields of view of images taken by the device 102. The image guidance module 106 provides quantification for progress which can compare a length of isolated vessel to a desired length to determine when sufficient progress has been achieved.

The image guidance module 106 guides the robot system 108 along the length of the target anatomy 131. In one embodiment, the device 102 is guided using the points of interest assigned during the planning stage.

Workstation 112 includes a display 118 for viewing internal images of a subject (patient) or volume and may include images with an overlay or other rendering generated over images collected from the device 102. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

Figure 2:
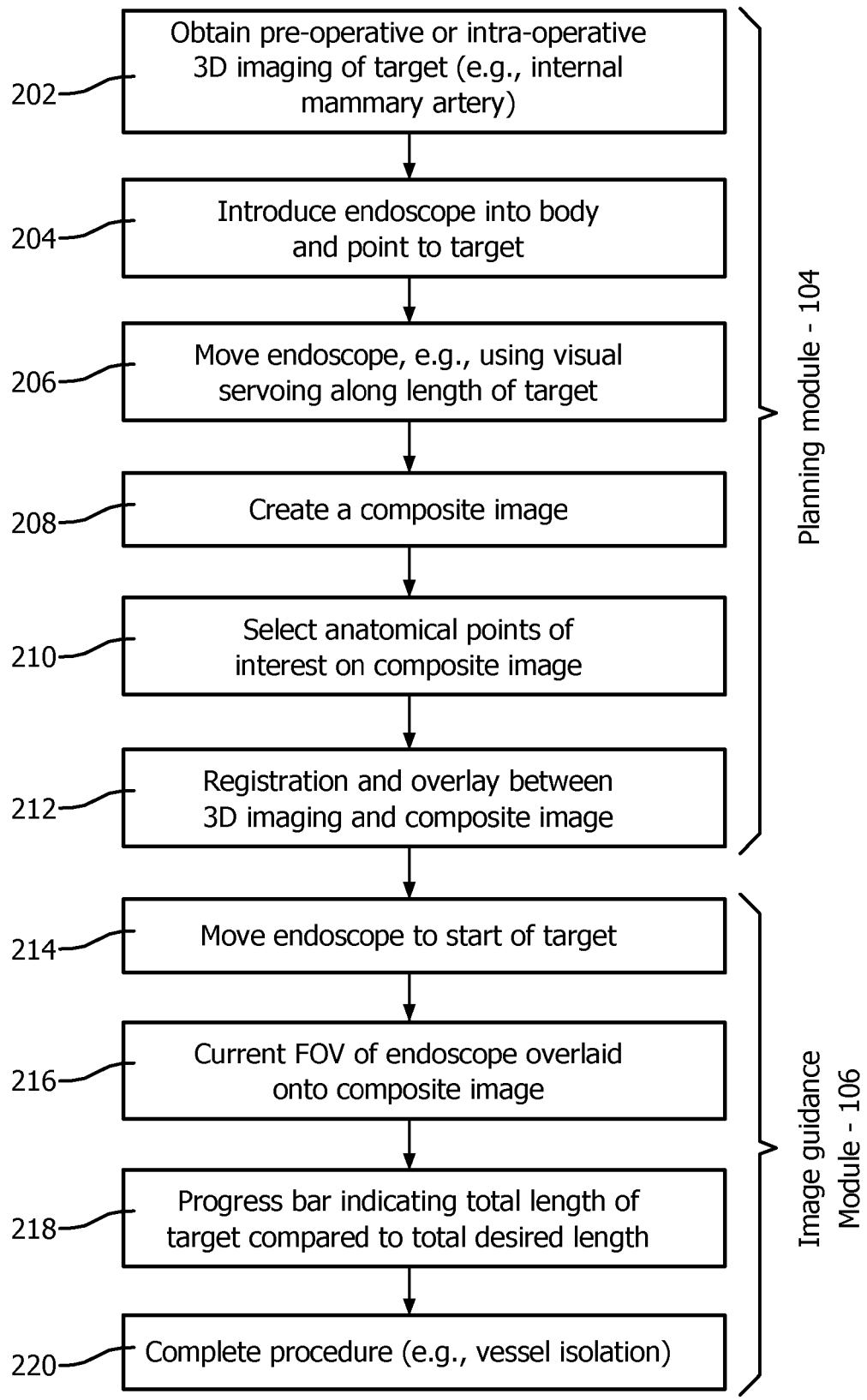
FIG. 2 is a block/flow diagram showing a system for visualizing an anatomical target in accordance with one embodiment.
Figure 3:
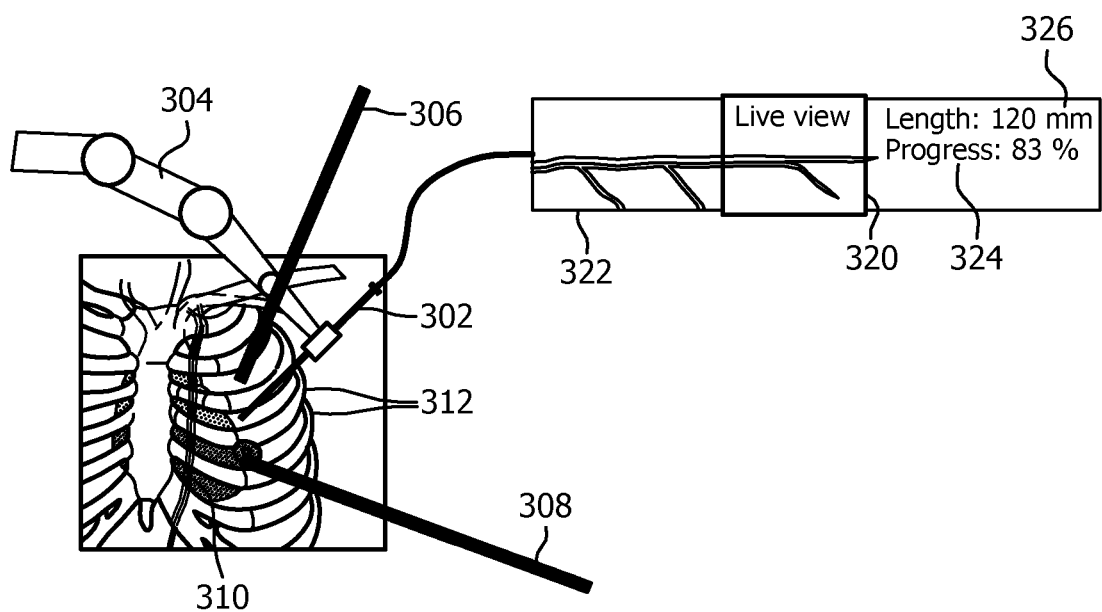
FIG. 3 is a diagram showing a system setup for conducting a blood vessel takedown and/or a coronary bypass in accordance with one illustrative embodiment.

Referring to FIG. 2, a method for performing a procedure in accordance with the present principles includes two parts. A first part of the procedure is performed by the planning module 104 and a second part is performed by the image guidance module 106 to facilitate vessel isolation. The planning module 104 performs steps 202 through 212. The image guidance module 106 performs steps 214 through 220. During the procedure, an intra-operative setup shown in FIG. 3 is employed. In other embodiments, some or all of the tasks in FIG. 2 may be shared or performed by a different module (104 and/or 106).

Referring to FIG. 3 with continued reference to FIG. 2, an endoscope 302 is held by a robotic system 304 while two instruments 306 and 308 are employed to isolate an IMA 310 and are held by a surgeon. The endoscope 302 is inserted in the chest cavity through a port (not shown), which permits access between ribs 312. This differs from a conventional setup where an assistant holds the endoscope. The robotic system 304 (endoscope holder) permits complete control by the surgeon over visualization by issuing commands based on the images provided.

In block 202, pre-operative or intra-operative images are obtained for a target area. Preoperative image may include volume images taken of a patient in advance. This may include computed tomography (CT) imaging, magnetic resonance imaging (MRI), or any other imaging modality. Intraoperative images may include X-ray imaging, direct photography (e.g., through an endoscope camera), etc. In block 204, the endoscope 302 is inserted into the chest. In block 206, the endoscope is moved into position to provide a useful field of view. In one embodiment, the endoscope is maneuvered using a technique called visual servoing, which includes centering the endoscope view on an area of interest during the procedure. Other endoscope movement techniques may be employed.

Figure 4:
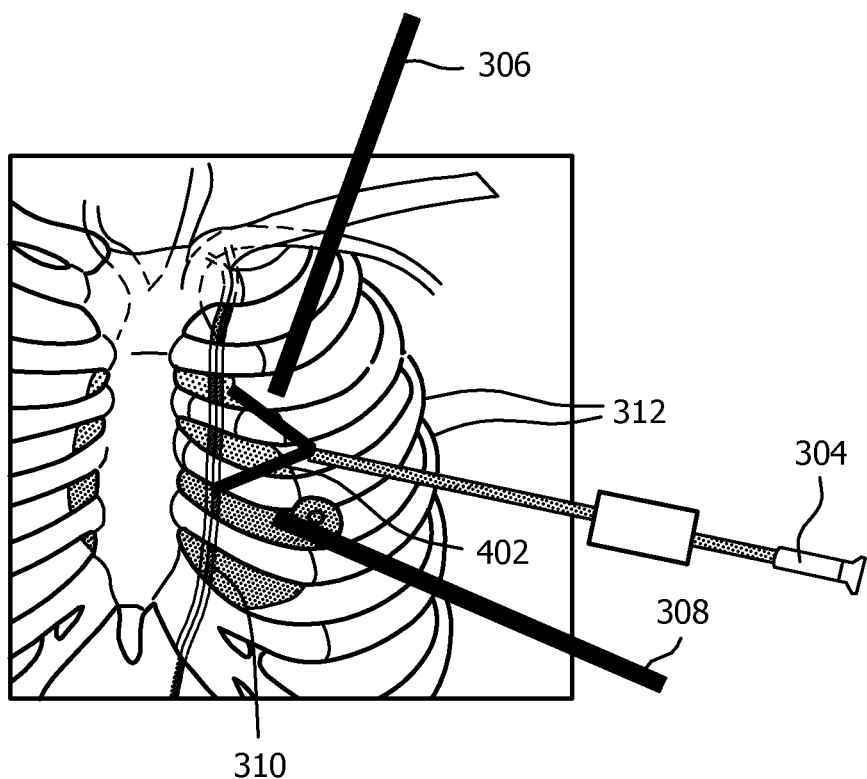
FIG. 4 is a diagram showing the system setup of FIG. 3 having an endoscope with a field of view less than that of the entire blood vessel to be taken down in accordance with one illustrative embodiment.

In block 208, a composite image of a target blood vessel is collected. Since a field of view of the endoscope is limited, images along a target blood vessel may be collected and stitched together to form a composite image of an entire target area, e.g., the IMA. FIG. 4 illustratively depicts a field of view (FOV) cone 402 for the endoscope 302 taking an image for the composite image.

In block 210, anatomical points of interest are selected on the composite image. These points may include regions where branches occur from the IMA, or regions of healthy or unhealthy tissue, scarred tissue, etc. The points of interest may be employed as address locations for focusing or moving the endoscope robotically at different times in the procedure. In block 212, registration is made between the pre-operative or intra-operative images, and the composite image that is gathered from the endoscope.

In block 214, the endoscope 302 (or at least the field of view of the endoscope) is moved to an initial position. This position is selected as an initial scan position and is preferably set at an end of a region of interest. In block 216, a current field of view of the endoscope 302 is overlaid over a corresponding portion of the composite image. The current field of view is depicted in FIG. 3 in box 320. A composite image 322 is overlaid by the live view image 320. In block 218, a progress bar is implemented showing a progress length against a total length as portions of the blood vessel are isolated. For example, as the composite image is traversed, the portion of the total length that is isolated is indicated or calculated as a percentage or number of branches sealed off. In FIG. 3, a total length 326 is shown, and a progress length 324 is indicated. In block 220, the progress continues until completion.

Referring to FIGS. 5-8, illustrative images of an IMA are shown to more fully describe the present embodiments. The present examples are illustrative, and it should be understood that the present principles may be applied to any surgical procedure or any system/method for reviewing or analyzing internal structures (e.g., in training systems, for ancient artifacts, mechanical systems, such as an engine block, etc.

Figure 5:
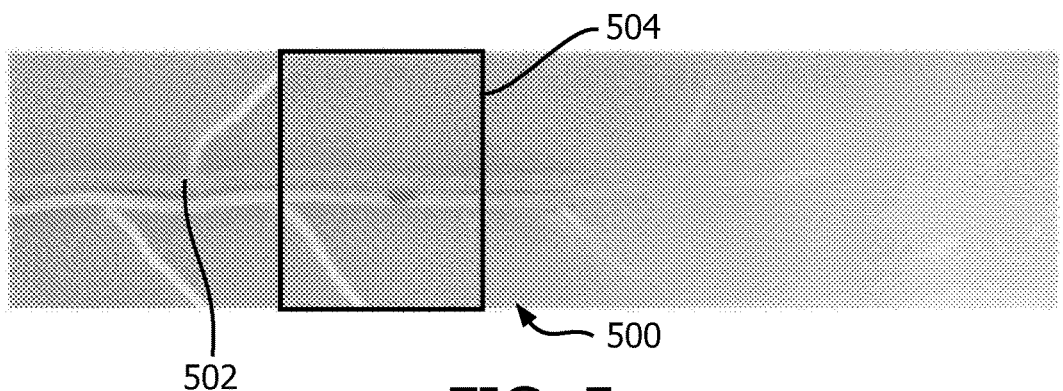
FIG. 5 is an image showing a composite image of stitched together fields of view from endoscopic video of an internal mammary artery in accordance with one embodiment.

Referring to FIG. 5, image stitching for a wide field of view image is illustratively depicted. With the endoscope in place and located towards a beginning of the LIMA vessel, a surgeon can start the acquisition of a wide field of view. To do so, the surgeon or a robot moves the endoscope using uncalibrated robotic visual servoing or other technique along the visible portion of the LIMA. In this way, the surgeon selects points along the LIMA, and the endoscope moves accordingly. The surgeon can also use a surgical instrument as a guide, as the instrument moves, and then the endoscope can follow the tool tip. This step is analogous to clinical practice, where the endoscope is moved either by an assistant or surgeon to observe the entire length of artery.

To stitch the images collected by the moving endoscope, known methods used to perform stitching of the images may be modified. The images may employ matching algorithms or other image processing techniques. One modification relates to the endoscope type. In this embodiment, the endoscope can be both oblique and forward viewing. A second modification relates to the motion of the endoscope. The motion of endoscope may be pre-programmed and gated by an image processing module 148 (FIG. 1). In this embodiment, the motion is generated and gated by the surgeon's commands. Another modification may involve the use of a flexible endoscope.

Although the motion is defined by the user, the verification of images used for stitching can be performed by optimizing captured images based on the amount of overlap and residual error in RGB values of overlapped pixels. Images are aligned to form a composite image 500. The composite image 500 includes an entire length of the blood vessel (e.g., IMA). A total length of the blood vessel may be computed from the image (using a scale or reference) or may be computed based upon a distance traveled by the endoscope or other tool in the images. The final result is the composite image 500 which includes a series of images (field of view images 504) along the length of IMA 502, which have been stitched together from individual images acquired by the endoscope over a time period.

Figure 6:
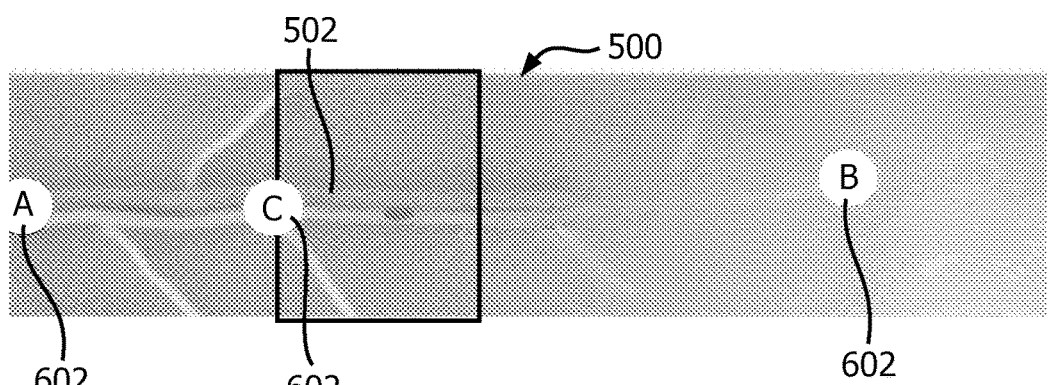
FIG. 6 is an image showing the composite image with points of interest assigned in accordance with one embodiment.

Referring to FIG. 6, the composite image 500 is shown with points of interest 602 selected and indicated. Once the composite image 500 of a relevant part of the IMA 502 has been generated, several anatomical points of interest 602 on the composite image 500 can be selected to plan for vessel isolation. These points 602 can be stored (by overlaying them on the image), and then referred to during the procedure. Alternately, as the points 602 are selected, the robotic endoscope holder moves the endoscope to that location, and the joint positions of the robot are stored, so they can be referred to during the image guided isolation procedure.

In the example of FIG. 6, the selection of points on the anatomical points of interest 602 include, e.g., an initial point of isolation marked "A", an end point of isolation marked "B" and a large bifurcation marked "C".

Referring to FIG. 7, in addition (or alternatively) to the selection of points on the composite image 500, the composite image 500 can be used to register a 2D endoscope image and preoperative or intraoperative 3D imaging. An overlay 702 of vasculature from 3D preoperative image is placed on the composite image 500. A comparison with the IMA 502 can indicate the location of bifurcations that are not directly visible on the endoscope images, as they could be located underneath fascia and other tissue.

Referring to FIG. 8, the image guidance module 106 is employed to guide the endoscope. The surgeon moves the endoscope back to a proximal position, e.g., close to the aorta, and starts performing the isolation of the artery from the surrounding tissue to detach the artery (IMA) from the chest wall. The surgeon can automatically locate the endoscope at that location by using visual servoing and/or referring to the previously selected points 602 (selected during the planning). As the surgeon progresses along the artery, both a current endoscope view which is overlaid in box 802 and the previously computed composite image 500 are displayed to the surgeon (with an optional artery overlay (702), e.g., from preoperative images).

The "picture in a picture" view permits the surgeon to observe a much wider field of view than what is currently available. In addition, as the motion of the endoscope is known from robot encoders combined with the registration information, a scale can be retrieved, showing the length of the portion of artery that is already isolated. A progress indicator 804, which may be a number or graphic, shows an amount of takedown of an artery as a portion of a desired or total length 806. The progress indicator 804 can be shown in the image on a display. In another embodiment, a progress bar may be shown instead of a percentage so that where the live view box 802 is overlaid on the composite image 500 as the surgeon advances across the IMA branch indicated as a portion of the total length of the vessel removed as compared to the desired or total length. The planning module (104, FIG. 1) may use pre-operative images to permit an estimation of the total length of the vessel, which can be used to generate the progress bar during the intervention with the scope.

In interpreting the appended claims, it should be understood that:
 a) the word "comprising" does not exclude the presence of other elements or acts than those listed in a given claim;
 b) the word "a" or "an" preceding an element does not exclude the presence of a plurality of such elements;
 c) any reference signs in the claims do not limit their scope;
 d) several "means" may be represented by the same item or hardware or software implemented structure or function; and
 e) no specific sequence of acts is intended to be required unless specifically indicated.

Having described preferred embodiments for enhanced visualization of blood vessels using a robotically steered endoscope (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system, comprising:
a first imaging device configured to generate a plurality of limited field of view images of an anatomical target as the first imaging device is moved along the anatomical target in a body;
a processor coupled to memory having stored instructions, and the instructions, when executed by the processor, cause the processor to:
receive a first set of the plurality of limited field of view images of the anatomical target from the first imaging device as the first imaging device is initially moved along the anatomical target,
stitch the first set of the plurality of limited field of view images of the anatomical target together to generate a composite image of the anatomical target,
overlay on the composite image of the anatomical target one of an intraoperative image of the anatomical target or a pre-operative image of the anatomical target, wherein the one of the intraoperative image of the anatomical target or the pre-operative image of the anatomical target is produced by a second imaging device which is disposed outside the body,
receive a second set of the plurality of the limited field of view images of the anatomical target from the first imaging device as the first imaging device is subsequently moved along the anatomical target, and
display the second set of the plurality of limited field of view images of the anatomical target as live video overlaid on the composite image of the anatomical target; and
a progress indicator displayed with the composite image of the anatomical target to indicate movement progress of the first imaging device along the anatomical target relative to a total length of the anatomical target, wherein the anatomical target includes a blood vessel to be isolated and the progress indicator includes at least one of a percentage of movement progress and a progress graphic to indicate an isolated portion of the blood vessel relative to a total length of the blood vessel.

2. The system of claim 1, wherein the instructions, when executed by the processor, further cause the processor to select at least one point of interest in the composite image of the anatomical target based on the one of the intraoperative image of the anatomical target or the pre-operative image of the anatomical target.

3. The system of claim 2, further comprising: a robot configured to guide the first imaging device, and wherein the instructions, when executed by the processor, further cause the processor to employ the at least one point of interest for guiding the first imaging device.

4. The system of claim 1, wherein the one of the intraoperative image of the anatomical target or the pre-operative image of the anatomical target is the pre-operative image of the anatomical target, and wherein the instructions, when executed by the processor, further cause the processor to employ the pre-operative image of the anatomical target including the blood vessel to estimate the total length of the blood vessel.

5. The system of claim 1, wherein the blood vessel is an internal mammary artery for use in bypass surgery.

6. The system of claim 1, wherein the first imaging device is a flexible endoscope.

7. The system of claim 1, wherein the one of the intraoperative image of the anatomical target or the pre-operative image of the anatomical target is a pre-operative computed tomography image of the anatomical target.

8. The system of claim 1, wherein the one of the intraoperative image of the anatomical target or the pre-operative image of the anatomical target is a pre-operative magnetic resonance image of the anatomical target.

9. The system of claim 1, wherein the one of the intraoperative image of the anatomical target or the pre-operative image of the anatomical target is an intraoperative X-ray image of the anatomical target.

10. The system of claim 1, wherein the one of the intraoperative image of the anatomical target or the pre-operative image of the anatomical target is an intraoperative acoustic image of the anatomical target.

* * * * *